(12) United States Patent
Araki et al.

(10) Patent No.: US 10,487,716 B2
(45) Date of Patent: Nov. 26, 2019

(54) PARTICULATE MATTER DETECTION APPARATUS

(71) Applicant: DENSO CORPORATION, Kariya, Aichi-pref. (JP)

(72) Inventors: Takashi Araki, Kariya (JP); Masayuki Tamura, Kariya (JP); Masahiro Yamamoto, Kariya (JP); Go Miyagawa, Kariya (JP); Toshihiro Sakawa, Kariya (JP); Masato Katsuno, Kariya (JP); Manabu Yoshidome, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 15/769,801

(22) PCT Filed: Oct. 21, 2016

(86) PCT No.: PCT/JP2016/081276
§ 371 (c)(1),
(2) Date: Apr. 20, 2018

(87) PCT Pub. No.: WO2017/069241
PCT Pub. Date: Apr. 27, 2017

(65) Prior Publication Data
US 2018/0306087 A1    Oct. 25, 2018

(30) Foreign Application Priority Data
Oct. 21, 2015    (JP) .................................. 2015-207175

(51) Int. Cl.
*F01N 11/00*    (2006.01)
*F01N 3/18*    (2006.01)
(Continued)

(52) U.S. Cl.
CPC ................ *F01N 11/00* (2013.01); *F01N 3/00* (2013.01); *F01N 3/023* (2013.01); *F01N 3/18* (2013.01);
(Continued)

(58) Field of Classification Search
CPC ...... F01N 9/002; F01N 11/00; F01N 2560/05; F01N 2560/20; F02D 41/1466; F02D 41/1494; F02D 41/222
See application file for complete search history.

(56) References Cited

U.S. PATENT DOCUMENTS

2008/0265870 A1    10/2008 Nair et al.
2011/0314796 A1    12/2011 Nakamura et al.
(Continued)

FOREIGN PATENT DOCUMENTS

DE    102010038613 A1 *    2/2012    ......... F02D 41/1466
JP    59-197847    11/1984
(Continued)

OTHER PUBLICATIONS

Machine translation of DE-102010038613-A1, accessed Jul. 8, 2019. (Year: 2019).*
(Continued)

*Primary Examiner* — Jonathan R Matthias
(74) *Attorney, Agent, or Firm* — Nixon & Vanderhye P.C.

(57) ABSTRACT

A particulate matter detection apparatus is provided with an element portion onto which PM contained in exhaust gas of an engine adheres thereto. A heater which heats the element portion, a quantity detecting portion which detects a quantity of the PM based on electrical properties of the element portion and a temperature detecting portion which detects a temperature of the element portion. The apparatus is further provided with a first and second temperature controller. The first temperature controller heats the element portion using
(Continued)

a heater in a first period, which excludes a period in which PM adheres to the element portion based on a detected temperature of the element portion. The element portion is heated in a first temperature range to combust soluble organic fractions contained in the PM and resist melting of ash components contained in the PM. The first period excludes a period in which PM adheres to the element portion. The second temperature controller heats the element portion in the second temperature range, which is higher than the first temperature range using the heater, such that ash is combusted, based on a detected temperature of the element portion.

20 Claims, 10 Drawing Sheets

(51) Int. Cl.
*F01N 3/00* (2006.01)
*F01N 3/023* (2006.01)
*F01N 9/00* (2006.01)

(52) U.S. Cl.
CPC .......... *F01N 9/002* (2013.01); *F01N 2550/04* (2013.01); *F01N 2900/14* (2013.01); *F01N 2900/1602* (2013.01); *F01N 2900/1606* (2013.01); *Y02T 10/47* (2013.01)

(56) References Cited

U.S. PATENT DOCUMENTS

| | | |
|---|---|---|
| 2012/0031078 A1 | 2/2012 | Sakamoto et al. |
| 2012/0031169 A1 | 2/2012 | Sakamoto et al. |
| 2012/0186230 A1 | 7/2012 | Yahata et al. |
| 2015/0177204 A1 | 6/2015 | Bessen et al. |
| 2017/0268979 A1* | 9/2017 | Hormann .......... G01N 15/0606 |

FOREIGN PATENT DOCUMENTS

| | | |
|---|---|---|
| JP | B2-3757860 | 1/2006 |
| JP | 2012-037369 | 2/2012 |
| JP | 2014-134129 | 7/2014 |
| JP | 2016-037899 | 3/2016 |
| JP | 2016-170118 | 9/2016 |
| JP | 2017-040214 | 2/2017 |

OTHER PUBLICATIONS

Machine translation of JP 2014-134129 A, accessed Jul. 8, 2019. (Year: 2019).*

* cited by examiner

PARTICULATE MATTER DETECTION APPARATUS

CROSS-REFERENCE RELATED APPLICATION

This application is the U.S. national phase of International Application No. PCT/JP2016/081276 filed on Oct. 21, 2016 which designated the U.S. and claims benefit of priority of earlier Japanese Patent Application No. 2015-207175 filed on Oct. 21, 2015, the entire contents of each of which are hereby incorporated by reference.

BACKGROUND

Technical Field

The present disclosure is related to a particulate matter detection apparatus which detects particulate matter, and more particularly related to a particulate matter detection apparatus which detects a quantity of particulate matter contained in an exhaust gas of an internal combustion engine.

Background Art

Conventionally, an apparatus equipped with a particulate matter sensor is known. This apparatus detects particulate matter (referred to as PM hereinafter) contained in an exhaust gas of diesel engine. In this known apparatus an element portion of the particulate matter sensor is controlled in a predetermined temperature range for combustion of PM, after the particulate matter is detected, and PM which has accumulated on the element portion is removed by combustion (JPA-1). A control in which accumulated PM is removed is referred to as a regeneration control. In performing the regeneration control, a particulate matter sensor element may be continually used.

CITATION LIST

Patent Literature

[Patent Literature 1] JP2012-12960A

There is not only soot and soluble organic fraction (SOF) as main components which are contained in particulate matter, but also ash which is derived from engine oil and fuel is also contained. Ash components are insulating substances such as calcium sulfate and magnesium sulfate. The inventors of the present disclosure discovered that by controlling an element portion in a temperature range for the combustion of soot, melting of ash components and fusion onto the element portion occurs depending on a particle radius of the ash components, when the element portion is regenerated. Since a PM sensor detects an amount of PM on the basis of electrical features of the element portion, if ash components are fused onto the element portion, a function of PM detection may deteriorate or even be lost as a consequence.

In view of the above issues, the present disclosure aims to provide a particulate matter detection apparatus, in which fusion of ash components onto the element portion is suppressible.

Solution to Problem

Summary

The present disclosure is a particulate matter detection apparatus provided with an element portion onto which a particulate matter contained in an exhaust gas of an internal combustion engine is to be adhered, a heater heating the element portion, a quantity detecting portion detecting a quantity of the particulate matter on a basis of electrical features of the element portion, and a temperature detection portion detecting a temperature of the element portion. There is also provided a first temperature controller configured to heat the element portion in a first temperature range using the heater at a first period, based on the temperature detected by the temperature detecting portion. The first temperature range is defined as a range of combustion of soluble organic fractions contained in the particulate matter and resisting melting of ash components contained in the particulate matter and the first period is a period which excludes a period of the particulate matter adhering onto the element portion. A second temperature controller is also configured to heat the element portion in a second temperature range using the heater in a second period, based on the temperature detected by the temperature detecting portion. The second temperature range is defined as a higher temperature range than the first temperature range and a temperature range of the combustion of the soot contained in the particulate matter. The second period is a period which is after the first period and a period which excludes the period of the particulate matter adhering onto the element portion.

According to the present disclosure, in the first period, which excludes the period in which the particulate matter adheres to the element portion, the element portion is heated in the first temperature range in which soluble organic fractions being contained in the particulate matter are combusted and ash components being contained in the particulate matter are not diffused. Thereafter, in the second period, the element portion is heated in the second temperature range at the temperature which is higher than the first temperature range, and in which the soot contained in the particulate matter is combusted.

In general, once detection of particulate matter adhered onto the element portion is finished, the particulate matter is combusted and removed, and the element portion is regenerated. In this regard, the inventor discovered the soot contained in the particulate matter melts and ash components contained in the particulate matter diffuse onto the element portion, depending on a radius of the ash, when the element portion is heated at a temperature for combustion of soot being the major component of particulate matter. By heating the element portion in the first temperature range before the second temperature range, soluble organic fractions are combusted and become vapor before the soot is combusted. Next, with the vaporization of the soluble organic fractions, the ash components are released from the particulate matter without melting and fly off the sensor element. As a result, when the element portion is heated in the second temperature range, the ash components are released from the particulate matter. Also, fusion of the ash components onto the element portion is suppressed and combustion of soot may be achieved, even when the element portion is heated in the second temperature range, due to the release of ash components from PM. Additionally, by heating the sensor element in the first temperature range, a temperature of the element portion may become higher than a target temperature due to combustion heat when soluble organic fractions are combusted. However, since the ash components are kept at a lower temperature than a temperature in which melting thereof occurs, fusion of the ash components onto the element portion is suppressed.

In the accompanying drawings.

EMBODIMENTS

Each embodiment of a particulate matter detection apparatus (referred to as PM detection apparatus, hereon), which is adapted to an engine system mounted in a vehicle, will next be described with reference to the figures. It is to be understood that the same symbol is used in the figures for configuring parts which are the same or equal to each other in each of the embodiments.

First Embodiment

Figure 1:
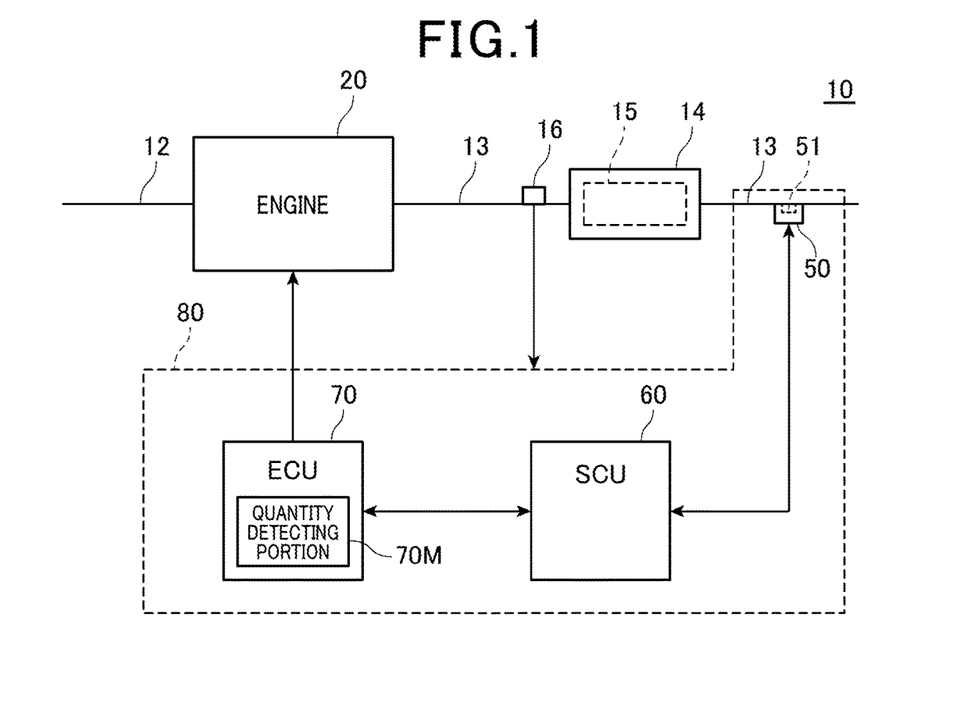
FIG. 1 is a diagram showing a schematic configuration of an engine system according to embodiments.

Firstly a configuration of an engine system 10 of a first embodiment is described. As shown in FIG. 1, the engine system 10 is provided with an engine 20. The engine 20 (internal combustion engine) is a diesel engine, for example. The engine 20A is connected to an intake passage 12 and an exhaust passage 13. An exhaust gas purifying device 14 is mounted on the exhaust passage 13. The exhaust gas purifying device 14 is configured to remove toxic components from exhaust gas, which is emitted from the engine 20. The toxic components are PM, for example, nitrogen oxides, and carbon compounds such as HC (hydrocarbons) and CO (carbon monoxide), which are generated from fuel that has not burned or from incomplete combustion. Particularly in the present embodiment, a PM capturing filter 15 is provided on the exhaust purification device 14. The exhaust gas purification device 14 is a known configuration, therefore further details are omitted.

The engine system 10 is equipped with a temperature sensor 16 and a PM detection apparatus 80. The temperature sensor 16 is disposed on an upstream-side of the exhaust passage 13, relative to the exhaust purification device 14, and is configured to monitor an exhaust gas temperature. An ECU (Electrical Control Unit) 70 described hereinafter monitors the exhaust gas purification device 14 and a state of the PM capturing filter 15, based on the exhaust gas temperature. If an amount of captured PM exceeds an allowed capacity, a regeneration control of the PM capturing filter is performed.

The PM detection apparatus 80 is provided with a PM sensor 50, an SCU60 (System Control Unit) and an ECU70. The PM detection apparatus 80 detects a quantity of PM which has passed through a PM capturing filter 15. PM includes soot and soluble organic fraction (Soluble Organic Fraction is referred to as SOF hereafter) as major components, and also includes ash components (referred to ash hereon). The ash is generated from, oxidated metal components, for example, which are contained in engine oil and fuel additive agents are oxidized to generate ash. As a further example, ash may be generated from, phosphorus, sulfur and calcium which have undergone oxidation. Soot which is the major component of PM is a substance which has conductivity, however ash is substance which has insulating properties.

Figure 3:
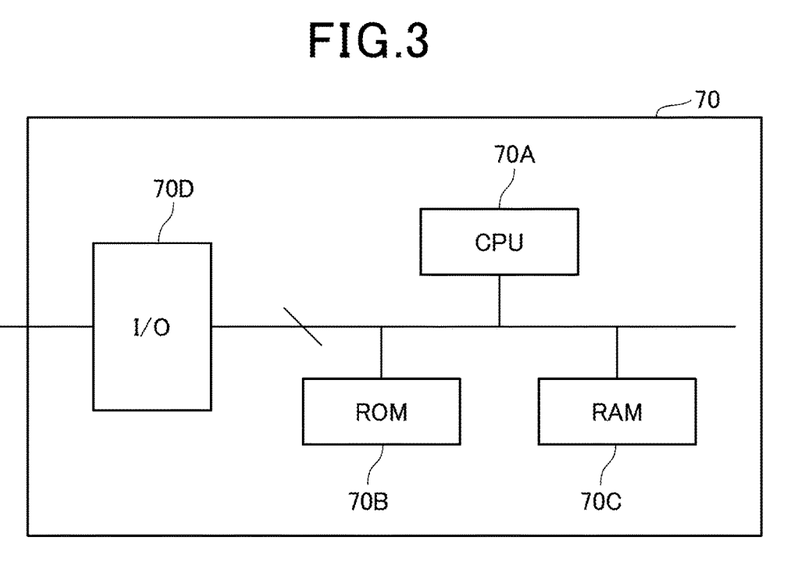
FIG. 3 is block diagram showing a schematic configuration of an ECU employed for each of the embodiments.

The PM sensor 50 is disposed on a downstream-side of the exhaust passage 13, relative to the exhaust gas purification device 14, and is configured to detect PM which slips through the PM capturing filter 15 and passes downstream thereof. Hereafter, a configuration of the PM sensor 50 will be described with reference to FIG. 3 and FIG. 4. The PM sensor 50 is provided with a sensor portion 40, a cover body 400, a cylindrical housing 500, and a cylindrical insulator 600. The cylindrical housing 500 is fixed to a passage wall of the exhaust passage 13. The cylindrical insulator 600 is maintained inside the cylindrical housing 500. The cover body 400 is formed with an empty inside, and is fixed to a lower-end portion of the cylindrical housing 500. The cover body 400 protrudes inside the exhaust passage 13. An upper half section of the sensor portion 40 is inserted into the cylindrical insulator 600 and fixed thereto. A respective lower half of the sensor portion 40 is positioned in the empty section of the cover body 400. Through holes 410 and 411 are provided on a respective bottom section and side section of the cover body 400, such that, the exhaust gas may flow into and out therefrom. The exhaust gas which contains PM is exhaust gas which has passed through the PM capturing filter 15.

Figure 5:
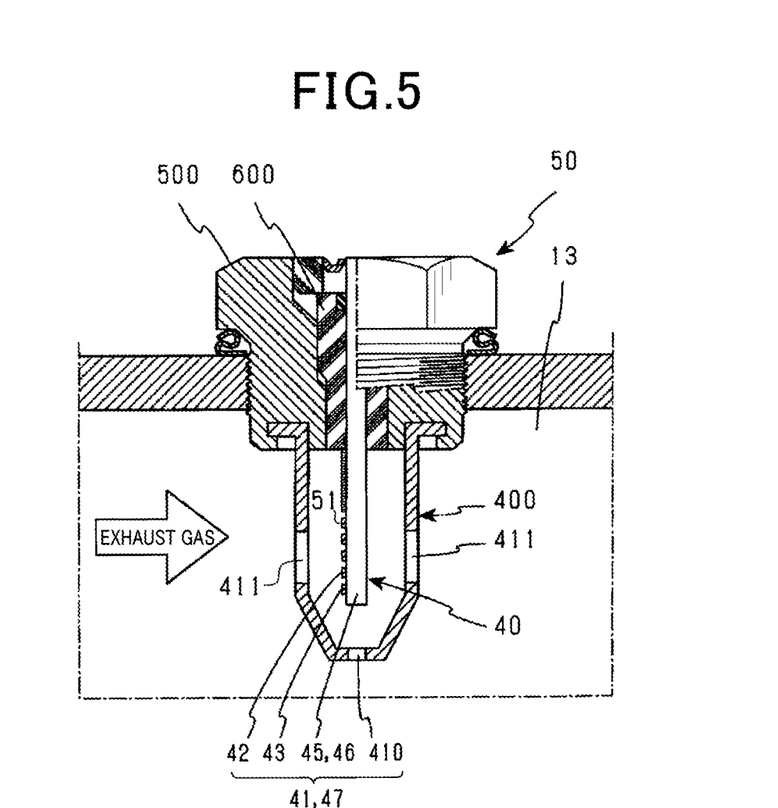
FIG. 5 is a schematic view showing a state in which the PM sensor is mounted onto an exhaust passage of an engine.

The sensor portion 40 of the PM sensor 50 is configured of the element portion 41 and the heater section 47. The element portion 41 is provided with one pair of comb shaped electrodes 42 and 43 formed on top of one surface 45a of an insulation substrate 45. The one pair of the electrodes 42 and 43 are arranged to oppose each other with a predetermined distance therebetween. In FIG. 5, the one pair electrodes are formed on side surface of the element portion 41, however one pair of electrodes may be formed on a front end side of thereof. The one pair of electrodes 42 and 43 are connected to the control circuit 61 of the SCU60. The insulation substrate 45 is formed from electrical insulating materials and ceramic material which have superior thermal resistance, for example, alumina, zirconia, beryllium oxide, mullite and silicon nitride. These materials are formed in a flat plate shape using known methods, for example, doctor blade method or press-forming method. The PM contained in the exhaust gas, which flows into the PM detection apparatus from the through holes 410 and 411, is adhered onto the element portion 41. Since a major component of PM is soot which has conductivity, an electrical resistance between the electrodes drops to a predetermined level, when the PM adheres between the electrodes 42 and 43 and a current flows. That is, once PM adheres between the electrodes, electrical properties of the element portion 41 are changed.

The heating section 47 is configured of the heater 44, which is formed on a top of one surface 46a of an insulation substrate 46. The insulation substrate 46 is formed by the same method used for the insulation substrate 45. The heater 44 is connected to a heater switch of the SCU60. The heating section 47 is disposed in a position directly below the electrodes 42 and 43. The heating section 47 efficiently heats the element portion in a predetermined temperature range. It is noted that the insulation substrates 45 and 46 may be unified into one. That is, a configuration in which the heater 44 is in-built in the insulation substrate 45 of the element portion 41, and the sensor portion 40 is configured only from the element portion 41 may also be provided.

The SCU 60 is equipped with a control circuit 61 and a heater switch 62. The heater switch 62 is a power source which supplies electricity to the heater 44. The control circuit 61 detects electrical resistance between electrodes 42 and 43, and transmits electric signals corresponding to the detected electrical resistance to the ECU 70. The control circuit 61 communicates with the ECU 70, in a proper manner, in order to mutually exchange information. The control circuit 61 controls operation of the heater switch 62, and controls a temperature of the heater 44. Specifically, the control circuit 61 is as computer system equipped with a CPU61A (Central Processing Unit), a ROM61B (Read Only Memory) and a and a RAM61C (Random Access Memory). The CPU61A serves to perform a main control process and the ROM61B stores a predetermined program, for example, and functions as a non-transitory recording media.

Figure 2:
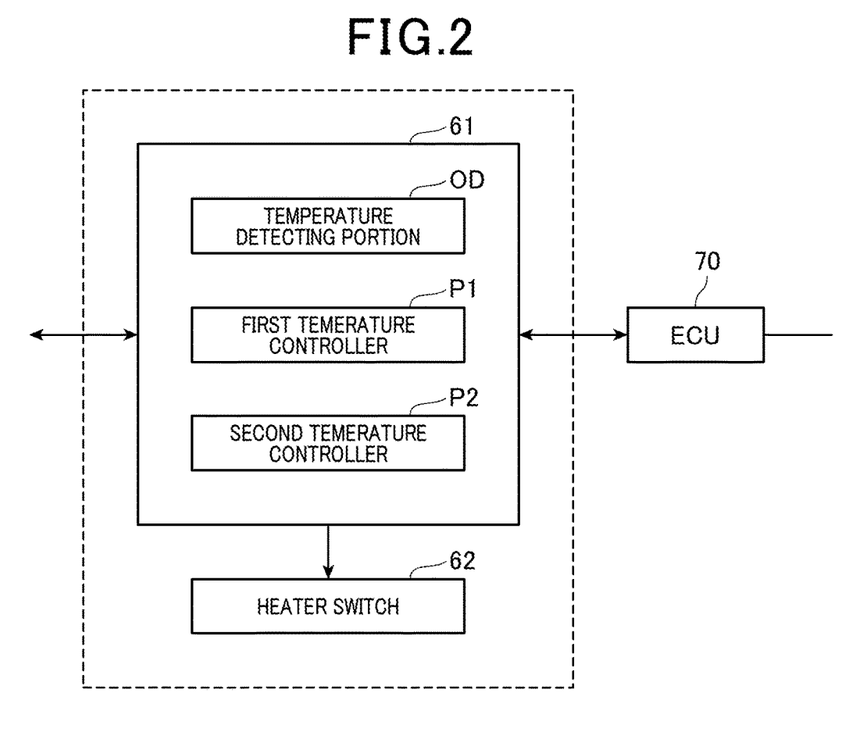
FIG. 2 is a functional block diagram exemplifying functions of a SCU.

The temperature detecting portion OD, the first temperature controller P1 and the second temperature controller P2 are functionally actualized by execution of a program which is executed by the CPU61A, the program of which is pre-stored in the ROM61B, as shown in FIG. 2. It is noted that, the RAM61C is used as a memory for temporary storage of data when the CPU61A executes the process.

The ECU70 is mainly configured of a CPU70A, and a ROM70B and a RAM70C memory, for example, and also a microcomputer equipped with an input/output interface I/O: 70D, for example, the configuration of which is the same as the control circuit 61. As was also described previously, the ROM70B functions as a non-transitory recording medium. The ECU70 actualizes a function of the quantity detecting portion 70M of which detects the quantity of PM, by execution of a detection process. The detecting process is provided by the CPU70A. The quantity detecting portion 70M detects the quantity of PM on the basis of the electrical properties of the element portion 41. That is, the detecting portion 70A detects the quantity of PM from a map, for example, which shows a correspondence between electric signals transmitted from the control circuit 61 and a quantity of PM. The ECU70 executes control of the engine 20 and the regeneration control of the PM capturing filter 15. It is noted that the CPU70A mounted on the ECU70 and the CPU60A mounted on the control circuit 61 functions in conjunction with each other to perform a process for temperature control which is described hereinafter in FIG. 7.

Next, a detailed operation of the PM detection apparatus 80 will be described with reference to the figures. If abnormality of the PM capturing filter occurs and it becomes difficult to capture PM in the usual manner, the quantity of PM emitted to the downstream side of the PM filter will suddenly increase. The ECU70 is configured to monitor the detected quantity of PM, at which point if the quantity of PM is clearly larger than the usual quantity, the ECU70 determines that the PM capturing filter 15 is abnormal. However, even if the PM capturing filter 15 is normal, once a quantity of PM accumulated on the element portion exceeds a given quantity, resistance between electrodes is decreased and a precision of PM detection will also decrease. Therefore, once the quantity of PM on the element portion has accumulated to a certain level, the accumulated PM is preferably combusted and removed by performing a sensor regeneration control.

A combustion temperature of soot which is the major component of PM is 600° C. or more, and if combustion is carried out at 750° C. or more, soot may be completely combusted and eliminated. A combustion temperature of SOF is generally 400° C. or more.

The melting point of ash is generally 900° C. or more. However, when ash has a particle radius of a few nanometers, the melting point thereof may decrease as a result of the so called quantum effect. Additionally, when a plurality of types of ash are mixed together, and a eutectic reaction occurs, the melting point of the ash may decrease. As a result, the melting point of the ash may decrease to 750° C., however, it is difficult for the ash melting point to decrease lower than 750° C. Additionally, due to the same effect, the melting point of the respective the soot and the soluble organic fractions may also decrease.

The inventors of the present disclosure discovered that by heating the element portion 41, between 750° C. and 850° C., for example, minute particles of ash melt and fusion of the ash onto the element portion occurs. Since the PM sensor 50 detects the quantity of PM on the basis of electrical properties of the element portion 41, once fusion of the insulating substances of ash onto the element portion 41 occurs, a sensitivity of the PM sensor 50 either deteriorates or is lost.

In contrast, when the element portion 41 is heated at a temperature between 600° C. and 750° C., combustion of the soot is incomplete, and remaining soot which is not completely combusted may be left on the element portion 41. Also, when the element portion 41 is heated at a temperature between 600° C. and 750° C., since soot and SOF are combusted at the same time, there is a concern of ash not properly flying off the element portion 41, and therefore situation of the ash residing on the element portion 41. In the first embodiment, heating of the element portion 41 is separated into two steps.

Each function of the control circuit 61 is described in detail hereafter.

A temperature detecting portion OD detects a temperature of the element portion 41. Specifically, the temperature detecting portion OD detects a temperature of the element portion 41 based on an electrical resistance value of the heater 44. Once power is supplied to heat the heater 44, the electric resistance value of the heater 44 is changed. There is a predetermined relationship between temperature of the heater 44 and the electric resistance value of the heater 44. As a result, the electrical resistance value of the heater 44 is determined by the SCU60, and the temperature detecting portion OD detects the temperature of the heater, from a correspondence relationship between a measured value of the electric resistance, a temperature which was prepared beforehand, and the electric resistance value. The temperature of the heater 44 is considered to be the temperature of the element portion 41.

Figure 4:
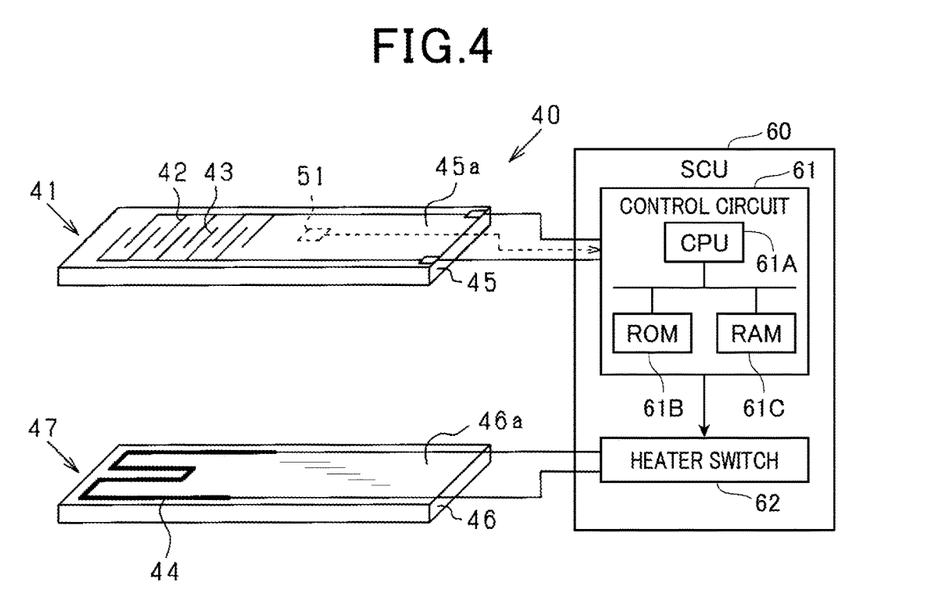
FIG. 4 is a schematic view of an element portion of a PM sensor and a heating section.

The element portion 41 is provided with a temperature sensor 51 (temperature detection apparatus), as shown with the broken line in FIG. 1, FIG. 4 and FIG. 5. The temperature of the element portion 41 may also be detected on the basis of a temperature which is detected by the temperature sensor 51. In providing the temperature sensor 51 on the element portion 41, the temperature of the element portion 41 may be detected with good precision.

The first temperature controller P1 heats the element portion 41 in the first temperature range for a first period by the heater 44 on the basis of a temperature detected by the temperature detecting portion OD. For example, the first temperature controller P1 feeds back the detected temperature of the element portion 41 and controls the temperature of the element portion 41 to a target temperature of the element portion 41 within the first temperature range. The first temperature range is a temperature range in which SOF is combusted and ash will not melt. That is, the first temperature range is from 400° C. to 600° C. A PM detection period is a period in which PM adhered to the element portion 41 is gathered.

Figure 6:
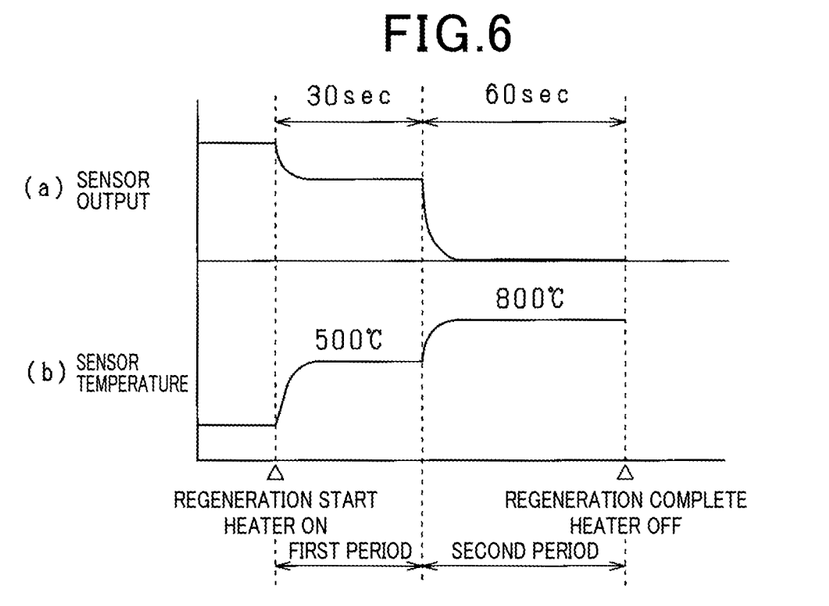
FIG. 6 is a time chart showing a sensor output (same FIG. 6 (a)) and a sensor temperature (same FIG. 6 (b)) when a regeneration control of the PM sensor is performed according to a first embodiment.

Additionally, as shown in FIG. 6 (b), the first temperature controller P1 controls the target temperature to a constant temperature in the first temperature range. Specifically, the first temperature controller controls the temperature of the element portion 41 in order to maintain the temperature at 500° C., for example. As a result, the element portion 41 may be maintained at an appropriate temperature, according to a condition of the first temperature range.

The first temperature range from 400° C. to 600° C. is a lower temperature range than the ash melting point, even when the melting point becomes low. When the element portion 41 is heated in the first temperature range, the SOF is combusted before the soot is combusted and the temperature of the element portion 41 may become higher than the target temperature, due to heat from the combustion of SOF. However, since there is a sufficient margin between an upper limit value of the first temperature range and a lower limit value of the ash melting point, the temperature of the element portion 41 is kept at a lower temperature than the ash melting point, even when the temperature of the element portion increases to a higher temperature than the target temperature due to combustion heat. As a result, when the element portion 41 is heated in the first temperature range, the SOF is combusted and vaporized and ash is released from PM and is released the element portion 41, without fusing onto the element portion 41.

The first temperature range is frequently higher than a temperature of the exhaust gas. For example, the temperature of exhaust gas of a diesel engine is approximately 400° C. In the first temperature, range Ash moves away from the element portion 41 to a direction of the exhaust gas by thermophoresis force. As a result, by heating the element portion 41 in the first temperature range, SOF is combusted and ash is pulled away from the element portion 41.

In a first period, the electric resistance between the electrodes 42 and 43 is increased by the combustion of SOF, as shown in FIG. 6 (a). At the same time, an output of the PM sensor 50 decreases, however, since soot remains accumulated between the electrodes 42 and 43, the output of the PM sensor is not decreased to zero.

The second temperature controller P2 is a period in which a PM period is excluded. That is, in the second period which is after the first period, the element portion 41 is heated in the second temperature range to the second period by the heater 44 based on a temperature detected by the temperature detection section. For example, the second temperature controller P2 provides feedback of the detected temperature of the element portion 41, and controls the temperature of the element portion 41 to the target temperature of the second temperature range. The second temperature range is a range higher than the first temperature range, and also a temperature range in which soot is combusted. Specifically, the second temperature is from 750° C. to 850° C.

As was also described for the first temperature range P1, the second temperature controller P2 controls a constant target temperature in the second temperature range, and controls the temperature of the element portion 41 such that the temperature is maintained constant, for example, maintained at 800° C., for example as shown in FIG. 6 (b).

The second temperature range from 750° C. to 850° C. is a temperature range in which soot is completely combusted. By heating the element portion 41 between 750° C. to 850° C., soot which has accumulated on the element portion is combusted and the soot remaining on the element portion 41 which is not combusted is diminished. When proceeding to the second period, since ash is released from the PM, fusion of ash onto the element portion 41 is suppressed, even when the element portion 41 is heated in the second temperature range.

As shown in FIG. 6(a), since soot is combusted in the second period, the electrical resistance between the electrodes 42 and 43 is further increased to become in a non-conductive state, and an output of the PM sensor is decreased to zero.

The respective first period and second period are not periods in which water condensate exists in the exhaust passage 13, as with a start-up period of a cooling duration, but periods in which the exhaust passage 13 is dry. As a result, a concern of cracking of the element portion 41 occurring may be eliminated even when the element portion 41 is heated in the respective first temperature range and the second temperature range. Additionally, whether or not the exhaust passage 13 is dry may be determined from whether a predetermined time has passed from a start-up of the engine 20, for example.

Figure 7:
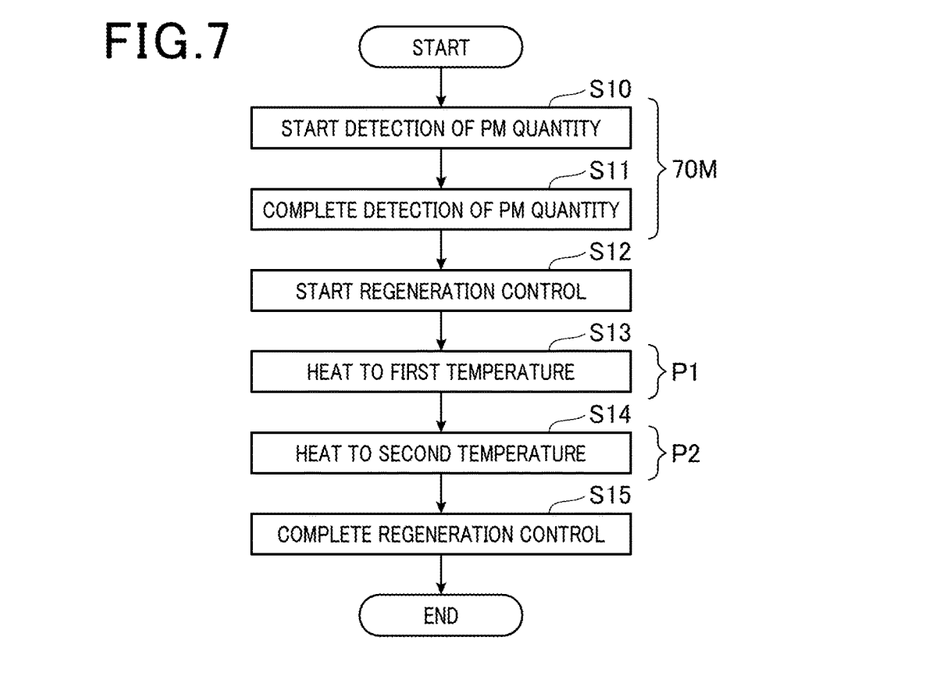
FIG. 7 is a flowchart showing a process order of the regeneration control of the PM sensor according to the first embodiment.

Next, a process order for the regeneration control of the PM sensor 50 according to the first embodiment will be described with reference to a flowchart shown in FIG. 7. This process is repeatedly performed at predetermined intervals, by collaboration of the ECU70, (specifically, CPU70A) and the SCU60 (specifically the CPU60A) during a period from when the engine 20 is started after the drying of the exhaust passage 13 is completed, until the engine 20 is stopped.

Firstly, in step S10, the detection of the quantity of PM adhered to the element portion 41 is started, with the heater 44 remaining off. Next, at step 11, the detection of the amount of PM adhered to the element portion 41 is completed (that is a function of the quantity detecting portion 70M is elicited) with the heater 44 switched off.

Next, at step S12, the heater 44 is switched on and the regeneration control of the PM sensor 50 is started. At step S13 (corresponding to the first temperature controller P1) power of the heater 44 is controlled and the element portion 41 is heated to a first temperature within the first temperature range in the first period. For example, the element portion is heated at 500° C. for 30 seconds. As a result, SOF which is contained on the PM is burned and ash is released the element portion 41.

Next, as step S14 (corresponding to the second temperature controller P2) the power of the heater 44 is controlled and the element portion 41 is heated to a second temperature within the second temperature range in the second period. For example, the element portion 41 is heated at 800° C., for 60 seconds. The soot which is contained in PM is thus combusted and PM which has accumulated on the element portion 41 is removed. Next, at step S15, the regeneration control is completed and the heater 44 is switched off.

The process in then ended. A process which begins from step S10 is re-started in the next process cycle.

Next, a result of a durability test of the PM sensor is described, when the regeneration control of the PM sensor 50 was performed according to the first embodiment, and when a conventional regeneration control was performed at a constant temperature. A first cycle of the durability test of the first embodiment entailed, a regeneration control of heating at 500° C. for 30 seconds+heating at 800° C. for 60 seconds, after which (→) the heater 44 was switched off for a period of 15 seconds cooling period (→) heater 44 off and PM detection for a period of 200 seconds (→) after PM detection, running (operation) for a period of 300 seconds (→return to regeneration control).

Conventionally, a cycle process of the durability test for the regeneration control entails heating at 800° C. for 60 seconds for the regeneration control of the process cycle according to the first embodiment. For both of the durability tests described above, PM was emitted from the engine 20 at an average concentration of 10 mg/m³ and a number of cycles of the durability test were compared until completion of the detection of PM was not achievable within the 200 seconds.

As a result, in the durability test related to the conventional regeneration control a sensitivity of the PM sensor 50 decreases after 110 cycles and the completion of the PM detection was not achievable within the 200 seconds. In contrast, in the durability test according to the first embodiment, the sensitivity of the sensor decreased after 160 cycles the completion of the PM detection was not achievable within 200 seconds. That is, by providing the temperature of the regeneration control as 2 steps, the fusion of ash onto the element portion 41 is suppressed and durability of the PM sensor 50 is improved, for the durability test according to the first embodiment.

Effects which are described hereafter may be obtained from the first embodiment.

(1) By heating the element portion 41 in the first temperature range before the second temperature range, SOF is combusted before soot is combusted. Also, with the combustion of SOF, ash is released from PM and is released the element portion 41. As a result, when the element portion 41 is heated in the second temperature range, whilst suppressing the fusion of ash onto the element portion 41 combustion of soot may also be achieved, even though the element portion 41 is heated in the second temperature range, since ash is released from PM.

(2) In providing the first temperature range from 400° C. to 600° C., the first temperature range becomes lower than the ash melting point, even when the ash melting point decreases. In addition to the first temperature range decreasing, the temperature may be kept as a lower temperature than the ash melting point, even when the temperature of the element portion 41 is higher than the target temperature due to combustion heat from the SOF combustion. Furthermore, ash may be moved away from the element portion 41 by the thermophoresis force. As a result, by providing the first temperature range from 400° C. to 600° C., melting of ash when the regeneration control is performed may be suppressed. Also, by providing the second temperature range from 750° C. to 850° C., soot may be reliably combusted in the second period.

(3) Since the first period and the second period are periods in which the exhaust passage 13 is dry, water-induced cracking of the element portion 41 may be prevented even when the element portion is heated in the first temperature range and the second temperature range.

(4) By controlling the temperature of element portion 41 in a constant temperature in the first temperature range and the second temperature range, the element portion 41 may be maintained at an appropriate temperature.

(5) There is a predetermined relationship between the temperature of the heater 44 and the resistance value of the heater 44, where the temperature of the heater 44 is considered to be the temperature of the element portion 41. The temperature of the element portion 41 may be therefore detected on the basis of the resistance value of the heater 44.

(6) In providing the temperature sensor 51 on the element portion 41, the temperature of the element portion 41 may be detected with good precision.

Second Embodiment

Next, a difference between the PM detection apparatus of the first embodiment and a second embodiment will be described hereafter. The temperature control of the element portion 41 of the respective first temperature controller P1 and the second temperature controller P1 of the PM detection apparatus 80 according to the second embodiment is different from the first embodiment.

Figure 8:
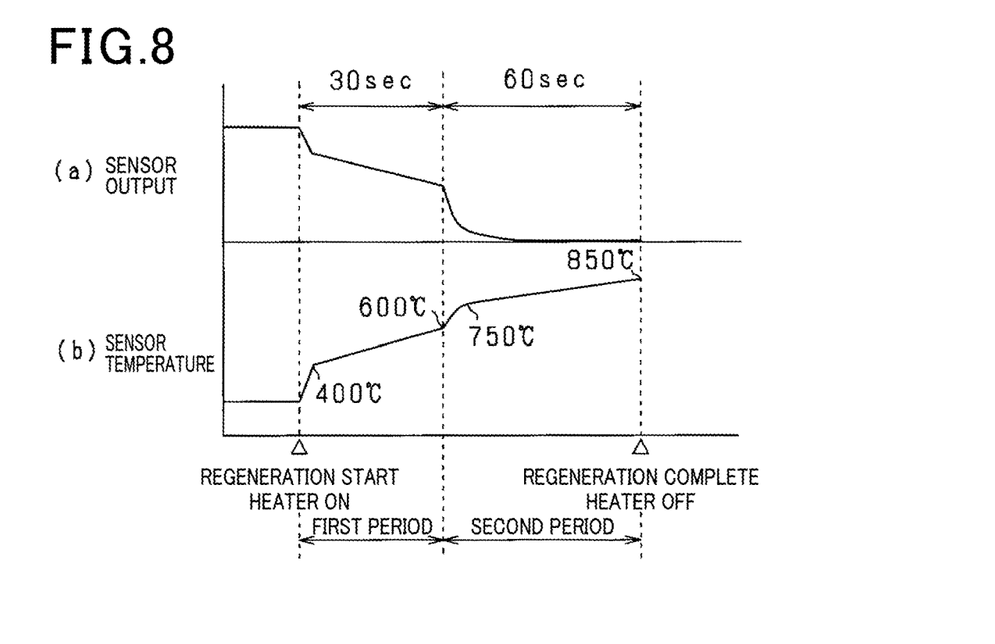
FIG. 8 is a time chart of a sensor output (same FIG. 8 (a)) and a temperature of a sensor (same FIG. 8 (b)) according to a second embodiment when the regeneration control of the PM sensor is performed according to a second embodiment.

More specifically, the first temperature controller P1 changes the target temperature in the first temperature range, in the first period, and controls the temperature of the element portion 41 such that the temperature thereof changes, as shown FIG. 8 (b). For example, the first temperature controller P1 gradually increases the temperature of the element portion 41 from 400° C. to 600° C. Additionally, the second temperature controller P2, changes the target temperature in the second temperature range, in the second period, and controls the temperature of the element portion 41 such that the temperature thereof changes, as shown FIG. 8 (b). For example, the second temperature controller P2 gradually increases the temperature of the element portion 41 from 750° C. to 850° C.

Once the temperature of the element portion 41 is gradually increased from 400° C. to 600° C. in the first period as shown in FIG. 8(b), an accumulated quantity of SOF gradually decreases, and the output of the PM sensor 50 gradually decreases, as shown in FIG. 8 (a). As a result, excessive heating from the combustion heat when SOF is combusted is reduced, and the fusion of ash onto the element portion 41 is suppressed to a greater extent than the first embodiment. As shown in FIG. 8 (b), if the temperature of the element portion 41 is gradually increased from 750° C. to 850° C. in the second period, an accumulated quantity of soot it smoothly decreased to a further extent than the first embodiment. As a result, the excessive heating from the combustion heat of when soot is combusted is decreased, and the fusion of ash onto the element portion 41 is suppressed to a greater extent than the first embodiment. Additionally, PM is eliminated and the output of the PM sensor decreases to zero as shown in FIG. 8 (a).

Figure 9:
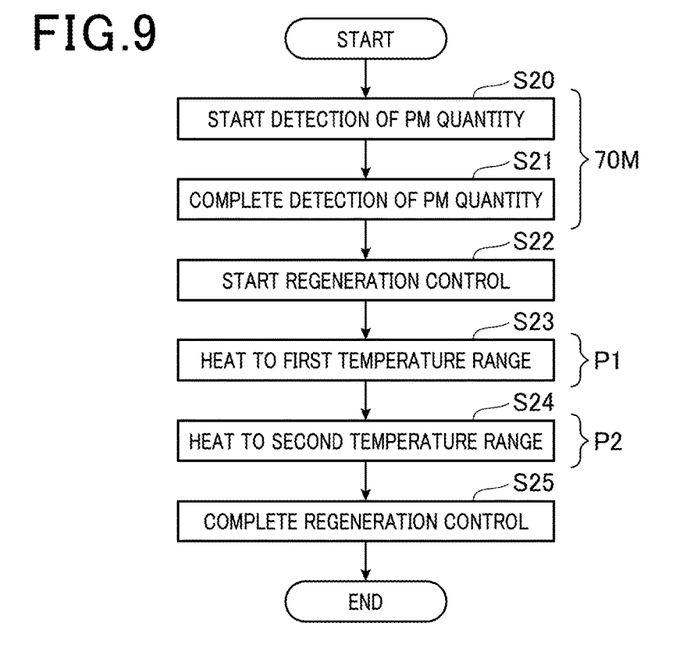
FIG. 9 is a flowchart showing the process order of the regeneration control of the PM sensor according to the second embodiment.

Next, a process order of the regeneration control of the PM sensor 50 according to the second embodiment is described with reference to the flow chart shown in FIG. 9.

This process is repeatedly performed at predetermined intervals, by collaboration of the ECU70, and the SCU60 during the period from when the engine 20 is started after the drying of the exhaust passage 13 is completed, until the engine 20 is stopped.

Firstly, the same process of step S10 to step S12 is also performed in step S20 to step S22.

Next, at step 23, the power of the heater 44 is controlled and the element portion 41 is variably controlled to a temperature within the first temperature range. For example, the element portion 41 is heated for 30 seconds, whilst changing the temperature thereof between 400° C. to 600° C. Next at step S24, the power of the heater 44 is controlled and the element portion 41 is variably controlled to a temperature in the second range. For example, the element portion 41 is heated for 60 seconds, whilst changing the temperature thereof between 750° C. to 850° C. Next at step S25, the regeneration control is ended, the heater 44 is switched off and this process ends.

In the second embodiment, as a result of performing the same durability test as the first embodiment, the sensitivity of the PM sensor 50 decreased after 180 cycles and completion of PM detection was not achievable within the 200 seconds. That is, according to the second embodiment, the durability of the PM sensor 50 is enhanced to a higher level than the first embodiment.

According to the second embodiment described hereinabove, the same effects described in (1) to (3) and (5) and (6) of the first embodiment are obtained. Also, fusion of ash onto the element portion is suppressed and the durability of the of the PM sensor 50 may be enhanced. By variably controlling the element portion 41 in the first temperature range and the second temperature range, the temperature control of the element portion 41 is easily performed, even when the temperature of the element portion 41 is variable due to an affect of the exhaust gas.

(A Modified Example of the Second Embodiment)

The element portion 41 may be heated at a constant temperature in one of the first temperature of the first period and the second temperature of the second period.

Third Embodiment

Next, a difference between the PM detection apparatus 80 of the first embodiment and a third embodiment will be described hereafter. The PM detection apparatus 80 according to the first embodiment starts the temperature control for the first temperature controller P1 in for every first period. In contrast, the PM detection apparatus 80 according to the third embodiment starts the temperature control of the first temperature controller P1 in the first period, only when a predetermined condition is satisfied.

More specifically, the first temperature controller P1 heats the element portion 41 in the first temperature range, when the condition of, the quantity of PM detected by the quantity detecting portion 70M reaches a predetermined threshold is satisfied. The larger the quantity of accumulated PM, the larger the quantity is of ash contained in the PM, and deterioration of the sensitivity of the PM sensor 50 is increased when the fusion of ash occurs. The PM accumulation refers to the PM which has accumulated on the element portion 41.

As a result, when the quantity of PM accumulated on the element portion 41 has satisfies the predetermined threshold, a decrease in the sensitivity of the PM sensor 50 is relatively large, when ash is fused onto the element portion 41. In view of this, the element portion 41 is heated in temperature ranges of two steps, for the regeneration control, which is the same as the first embodiment. However, if the quantity of PM which has accumulated is less than the predetermined threshold, the decrease in the sensitivity of the PM sensor 50 is relatively small, when ash is fused. The PM accumulation refers to PM which has accumulated on the element portion 41. For this reason, the element portion 41 is heated at a constant temperature in the same manner as the conventional regeneration control.

Whether the accumulated quantity of PM on the element portion 41 has reached the predetermined threshold is determined by to whether or not an output current of the PM sensor 50 is equal to higher than a value of a current threshold. The current threshold is 15 µA, for example. As shown with the solid line in FIG. 10 (a), when the accumulated quantity of PM is equal to or higher than the predetermined threshold, the output current of the PM sensor 50 is equal to or higher than the current threshold. In this case, as shown with the solid line id FIG. 10(b), in the first period of the regeneration control, the element portion 41 is heated for 30 seconds at 500° C., for example, and in the second period, the element portion 41 is heated at 800° C. for 60 seconds, for example.

Figure 10:
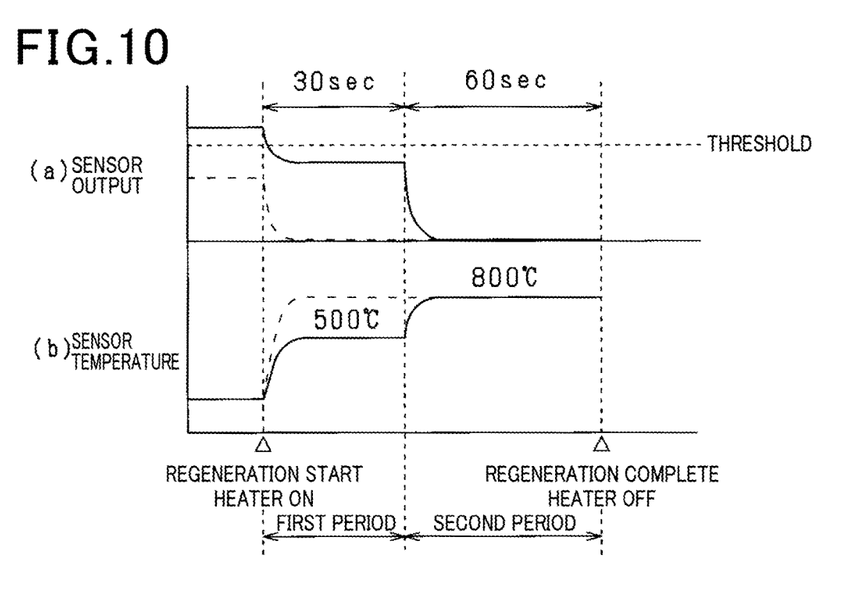
FIG. 10 is a time chart of the sensor output (same figure (a)) and the temperature of the sensor (same FIG. 10(b)) when the regeneration control of the PM sensor is performed according to a third embodiment.

As shown with the broken line in FIG. 10 (a), when the accumulated quantity of PM is less than the predetermined threshold, the output current of the PM sensor 50 is less than the current threshold. In this case, as shown with the broken line in FIG. 10 (b), the element portion 41 is heated at a constant temperature of 800° C. for 90 seconds, during a period of the regeneration control.

Figure 11:
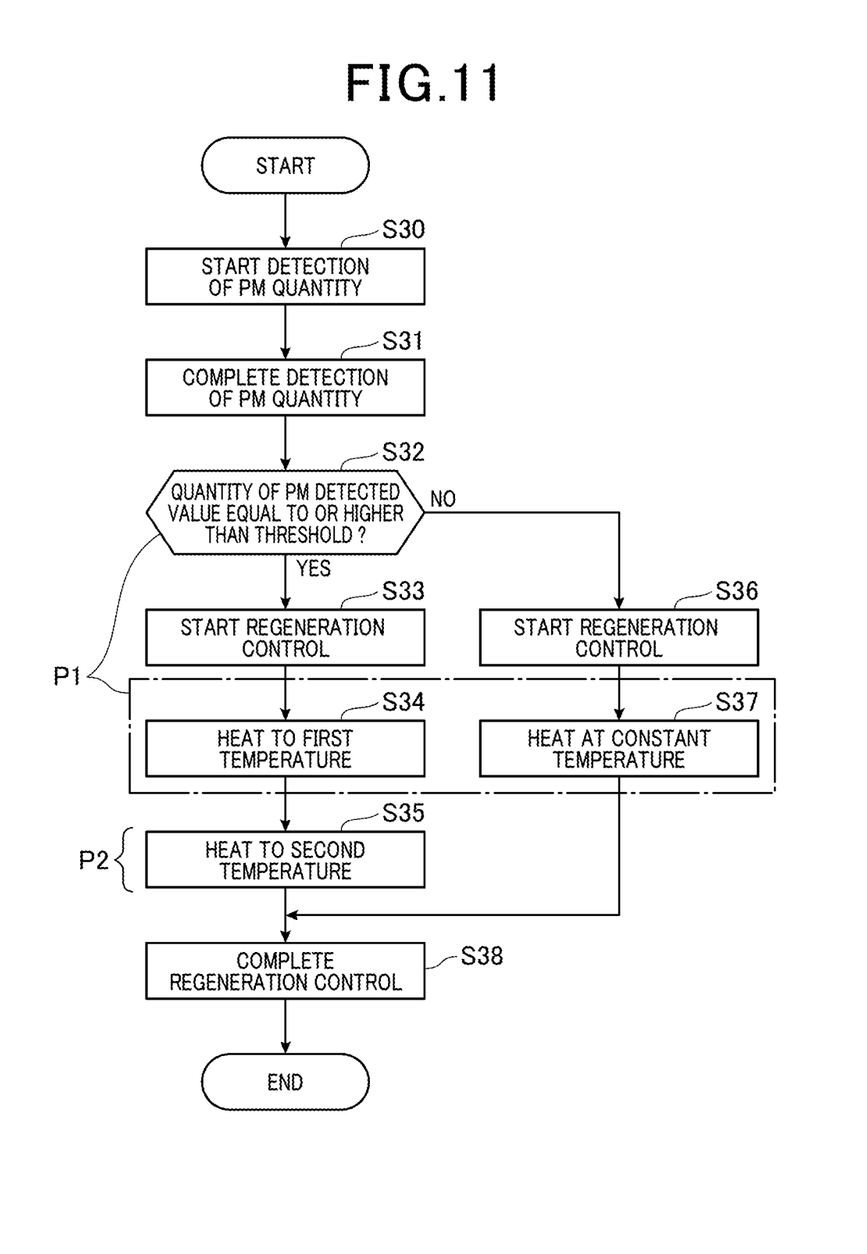
FIG. 11 is a flowchart showing the process order of the regeneration control of the PM sensor according to the third embodiment.

Next, a process order which is performed for the regeneration control of the PM sensor 50 according to a third embodiment is described, with reference to the flowchart of FIG. 11. This process is repeatedly performed at predetermined intervals, by collaboration of the ECU70, and the SCU60 during the period from when the engine 20 is started after the drying of the exhaust passage 13 is completed, until the engine 20 is stopped.

Firstly, the same process of step S10 and step S11 are also performed in step S30 and step S31.

Next, at step S32, it is determined whether a detected value of the PM quantity is equal to or higher than a threshold. That is, it is determined whether the output current of the PM sensor 50 is equal to or higher than the threshold current. At step S32, if the detected value of the PM quantity is determined to be equal to or higher than the threshold, the regeneration control of heating the element portion 41 in temperature range of two steps is preformed, such that the fusion of ash on the element portion 41 is suppressed. More specifically, the same process as step S12 and step S14 is also performed from step S33 to step S35. At step S38, the regeneration control is then ended, the heater 44 switched off and this process ends. It is noted that, the steps S32, S34 and S37 correspond to the first temperature controller, and the step S35 corresponds to the second heater controller P2.

In contrast, if the value of the detected quantity of PM is less than the predetermined threshold, it is determined that suppression of the fusion of ash on the element portion 41 is unnecessary, and the conventional regeneration control is performed. Specifically, at step S36, the heater 44 is switched on and the regeneration control is started, and as step S37 the element portion 41 is heated at a constant temperature. At step S38, the regeneration control is ended, the heater 44 switched off and this process ends.

According to the third embodiment described hereinabove, the same effects (1) to (6) of the first embodiment are obtained, and the regeneration control of heating the element portion 41 in the temperature range of two steps is performed, when the condition of the quantity of PM reaching a predetermined threshold is satisfied. As a result, when a relatively large decrease of the sensitivity of the PM sensor 50 is a concern due to the diffusion of ash onto the element portion 41, a process to suppress the fusion of ash onto the element portion 41 is performed. Furthermore, the fusion of the ash onto the element portion may be suppressed more effectively.

(A Modified Example of the Third Embodiment)

The control of the temperature of the element portion 41 in the first temperature range and second temperature range, as described in the second embodiment, may also be performed from step S33 and to step S35, such that the temperature of the element portion 41 is variable. On the other hand, the temperature of the element portion 41 may also be controlled in either one of the first temperature range and the second temperature range.

Fourth Embodiment

Next, a difference between the PM detection apparatus of the first embodiment and a fourth embodiment will be described. The temperature of the element portion 41 is variable by an affect of exhaust gas. In the fourth embodiment, the first temperature controller P1 and the second temperature controller P2 set a heating temperature of the element portion 41 on the basis of the exhaust gas information of the engine 20.

Specifically, the first temperature controller P1 sets the temperature of the heater 44 on the basis of the exhaust gas information. The exhaust gas information is the temperature of the exhaust gas and a speed thereof for example. The speed of the exhaust gas is calculated from an intake volume of the engine 20, an intake pressure, and cross sectional area of the exhaust gas passage 13, for example. The temperature of the element portion 41 changes due to the effect of the exhaust gas temperature, and the higher the speed of the exhaust gas is the larger the effect is of the exhaust gas temperature. For example, if the exhaust gas temperature is lower than the element portion 41, and the speed of the exhaust gas relatively high, the temperature of the element portion 41 easily decreases to a lower temperature than the heater 44. Therefore in this case, the first temperature controller P1 sets the temperature of the heater 44 higher than the target temperature of the element portion 41.

Also, the second temperature controller P2, sets the temperature of the heater 44 on the basis of the exhaust gas information, the same as the first temperature controller P1.

Figure 12:
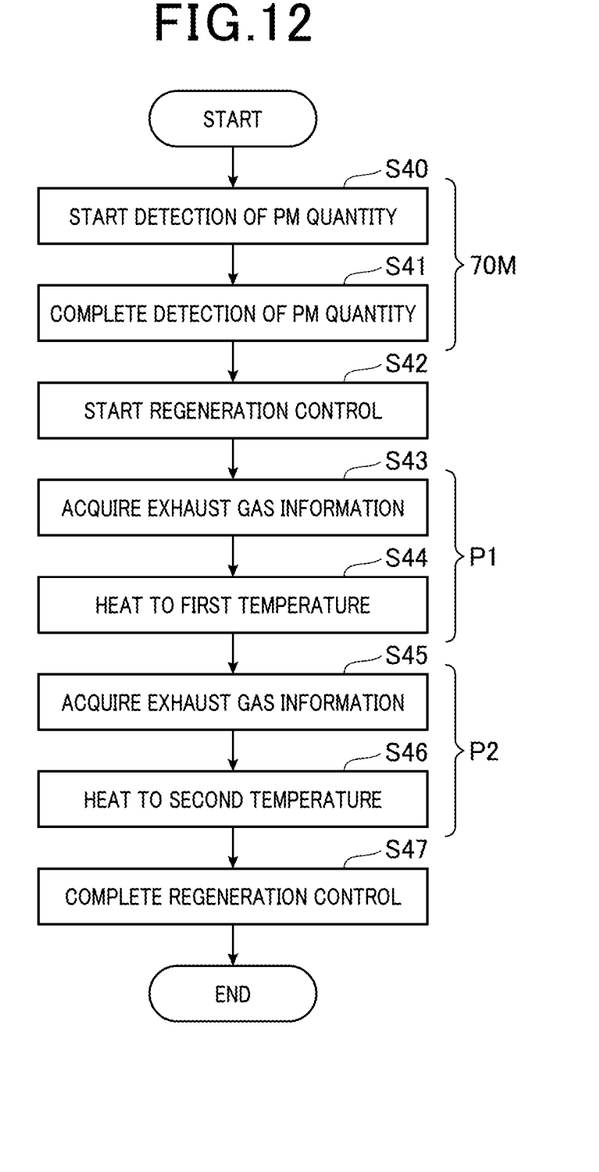
FIG. 12 is a flowchart showing the process order of the regeneration control of the PM sensor according to a fourth embodiment.

Next, the process order of the regeneration control of the PM sensor 50 according to the fourth embodiment is described with reference to the flowchart of FIG. 12.

This process is repeatedly performed at predetermined intervals, by collaboration of the ECU70 and the SCU60 during the period from when the engine 20 is started after the drying of the exhaust passage 13 is completed, until the engine 20 is stopped.

Firstly, the same process of step S10 to step S12 is also performed in step S40 to step S42.

Next, at step S43, the exhaust gas information, for example, the exhaust gas temperature and the exhaust gas speed is acquired. Next, at step S44, in order to heat the element portion 41 at the first temperature in the first temperature range, the temperature of the heater 44 is set and the element portion heated in the first period on the basis of the exhaust gas information acquired at step S43.

Next, at step S45, the exhaust gas information is acquired. Next, at step S46, in order to heat the element portion 41 at the second temperature in the second temperature range, the temperature of the heater 44 is set and the element portion heated in the second period on the basis of the exhaust gas information acquired at step S45

Next, at step S47, the regeneration control is finished, the heater 44 is switched off and this process ends.

According to the fourth embodiment described hereinabove, the same effects described in (1) to (6) of the first embodiment are obtained and by setting a heating temperature of the element portion 41 based on the exhaust gas information, the temperature of the element portion 41 may be controlled to the target temperature with good precision. Also, the fusion of ash onto the element portion 41 may be suppressed.

(Modified Example of the Fourth Embodiment)

At step S44 and step S46, the temperature of the element portion 41 may controlled such that the temperature is variable, in the first temperature range and the second temperature range, as was described in the second embodiment. On the other hand, the temperature of the element portion 41 may controlled so that the temperature is variable in either one of the first temperature range and the second temperature range.

A regeneration control in which the element portion is heated in the temperature range of two steps may be performed, when the condition of the detected quantity of PM has reached the threshold, as described in the third embodiment. The fourth embodiment may be combined with the second embodiment and the third embodiment in an appropriate manner.

Other Embodiments

The function of the control circuit 61 of the SCU60 is actualized by the ECU70, and the heater switch 62 may be incorporated in the ECU70. That is, the electrodes 42 and 43, and the heater 44 are directly connected to the ECU70, and the PM detection apparatus 80 may be configured from the PM sensor 50 and the ECU70. When the PM detection apparatus is provided with the SCU60 and the ECU70, the ECU70 may actualize a part of the function of the control circuit 61. In contrast, the control circuit 61 may actualize a part of the function of the ECU70. Also, the ECU70 may not perform the control of the engine 20.

A suitable engine which may use the PM detection apparatus 80 is not limited to a diesel engine. That is, the PM detection apparatus 80 may be applied to an engine which uses fuel, such as, gasoline, alcohol, or natural gas, for example.

SYMBOLS

20 . . . engine
41 . . . element portion
44 . . . heater
60 . . . SCU
70 . . . ECU

What is claimed is:
1. A particulate matter detection apparatus comprising;
an element portion onto which a particulate matter contained in an exhaust gas of an internal combustion engine is to be adhered;

a heater heating the element portion;
a quantity detecting portion detecting a quantity of the particulate matter on a basis of electrical features of the element portion;
a temperature detection portion detecting a temperature of the element portion;
a first temperature controller configured to heat the element portion in a first temperature range using the heater at a first period, based on the temperature detected by the temperature detecting portion, the first temperature range being defined as a range of combustion of soluble organic fractions contained in the particulate matter and resisting melting of ash components contained in the particulate matter, the first period being a period which excludes a period of the particulate matter adhering onto the element portion; and
a second temperature controller configured to heat the element portion in a second temperature range using the heater in a second period, based on the temperature detected by the temperature detecting portion, the second temperature range being defined as a higher temperature range than the first temperature range and a temperature range of the combustion of the soot contained in the particulate matter, the second period being after the first period and a period which excludes the period of the particulate matter adhering onto the element portion.

2. The particulate matter detection apparatus according to claim 1, wherein the first temperature range is from 400° C. to 600° C., and the second temperature range is from 750° C. to 850° C.

3. The particulate matter detection apparatus according to claim 2, wherein the first temperature control is provided with a determination section which determines whether the quantity of PM satisfies a predetermined threshold, the quantity of PM being detected by the quantity detecting portion; and
the first temperature controller heats the element portion in the first temperature range, when the determination section determines that the quantity of PM satisfies the predetermined threshold.

4. The particulate matter detection apparatus according to claim 2, wherein the first period and the second period are periods in which an exhaust passage of the internal combustion engine is dry.

5. The particulate matter detection apparatus according to claim 2, wherein the first temperature controller controls the temperature of the element portion in the first temperature range, such that the temperature of the element portion is maintained at a constant temperature.

6. The particulate matter detection apparatus according to claim 2, wherein the first temperature controller controls the temperature of the element portion in the first temperature range, such that the temperature of the element portion is variable.

7. The particulate matter detection apparatus according to claim 2, wherein the second temperature controller controls the temperature of the element portion in the second temperature range, such that the element portion is maintained at a constant temperature.

8. The particulate matter detection apparatus according to claim 2, wherein the second temperature controller controls the temperature of the element portion in the second temperature range, such that the temperature of the element portion is variable.

9. The particulate matter detection apparatus according to claim 2, wherein the first temperature controller sets a temperature of the heater based on exhaust gas information of the internal combustion engine.

10. The particulate matter detection apparatus according to claim 2, wherein the second temperature controller sets the temperature of the heater based on the exhaust gas information of the internal combustion engine.

11. The particulate matter detection apparatus according to claim 1, wherein the first temperature control is provided with a determination section which determines whether the quantity of PM satisfies a predetermined threshold, the quantity of PM being detected by the quantity detecting portion; and
the first temperature controller heats the element portion in the first temperature range, when the determination section determines that the quantity of PM satisfies the predetermined threshold.

12. The particulate matter detection apparatus according to claim 1, wherein the first period and the second period are periods in which an exhaust passage of the internal combustion engine is dry.

13. The particulate matter detection apparatus according to claim 1, wherein the first temperature controller controls the temperature of the element portion in the first temperature range, such that the temperature of the element portion is maintained at a constant temperature.

14. The particulate matter detection apparatus according to claim 1, wherein the first temperature controller controls the temperature of the element portion in the first temperature range, such that the temperature of the element portion is variable.

15. The particulate matter detection apparatus according to claim 1, wherein the second temperature controller controls the temperature of the element portion in the second temperature range, such that the element portion is maintained at a constant temperature.

16. The particulate matter detection apparatus according to claim 1, wherein the second temperature controller controls the temperature of the element portion in the second temperature range, such that the temperature of the element portion is variable.

17. The particulate matter detection apparatus according to claim 1, wherein the first temperature controller sets a temperature of the heater based on exhaust gas information of the internal combustion engine.

18. The particulate matter detection apparatus according to claim 1, wherein the second temperature controller sets the temperature of the heater based on the exhaust gas information of the internal combustion engine.

19. The particulate matter detection apparatus according to claim 1, wherein the temperature detecting portion detects the temperature of the element portion based on a resistance value of the heater.

20. The particulate matter detection apparatus according to claim 1, the apparatus further comprising
a temperature detection apparatus disposed on the element portion, wherein the temperature detecting portion detects the temperature of the element portion on the basis of a temperature detected by the temperature detection apparatus.

* * * * *